(12) United States Patent
Haddad et al.

(10) Patent No.: US 9,790,377 B2
(45) Date of Patent: Oct. 17, 2017

(54) SYNTHESIS OF FUNCTIONAL FLUORINATED POLYHEDRAL OLIGOMERIC SILSESQUIOXANE ("F-POSS")

(71) Applicant: The United States of America as Represented by the Secretary of the Air Force, Washington, DC (US)

(72) Inventors: Timothy S. Haddad, Lancaster, CA (US); Joseph M. Mabry, Lancaster, CA (US); Sean Ramirez, Lancaster, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 14/990,973

(22) Filed: Jan. 8, 2016

(65) Prior Publication Data
US 2016/0122558 A1 May 5, 2016

Related U.S. Application Data

(62) Division of application No. 13/624,151, filed on Sep. 21, 2012, now Pat. No. 9,249,313.

(Continued)

(51) Int. Cl.
*C07F 7/21* (2006.01)
*B05D 3/12* (2006.01)
(Continued)

(52) U.S. Cl.
CPC .......... *C09D 5/1662* (2013.01); *B05D 5/083* (2013.01); *C07F 7/21* (2013.01); *C09D 7/1233* (2013.01); *C08K 5/549* (2013.01)

(58) Field of Classification Search
USPC .......................... 524/261; 556/460; 427/240
See application file for complete search history.

(56) References Cited

U.S. PATENT DOCUMENTS

| 6,770,724 B1* | 8/2004 | Lichtenhan | C07F 7/0885 528/12 |
| 7,053,167 B2* | 5/2006 | Ito | C08G 77/045 528/31 |

(Continued)

FOREIGN PATENT DOCUMENTS

| WO | 2005068399 | 7/2005 |
| WO | 2007052260 | 5/2007 |

OTHER PUBLICATIONS

United States Patent and Trademark Office, Final Office Action in U.S. Appl. No. 14/013,600 dated Feb. 4, 2016, 6 pages total.

(Continued)

*Primary Examiner* — Mark Kaucher
*Assistant Examiner* — Henry Hu
(74) *Attorney, Agent, or Firm* — AFMCLO/JAZ; Chastity Whitaker (57) ABSTRACT

A method of manufacturing a fluorinated polyhedral oligomeric silsesquioxane. The method for manufacture includes opening a single edge of a closed-cage F-POSS and bridging the opened, single edge with a sulfate group. The sulfate group is converted to a disilanol, which is then reacted with a functional dichlorosilane having an organic functional group comprising at least three carbon atoms.

16 Claims, 7 Drawing Sheets

Related U.S. Application Data (60) Provisional application No. 61/537,122, filed on Sep. 21, 2011.

(51) Int. Cl.
  *C09D 5/16* (2006.01)
  *B05D 5/08* (2006.01)
  *C09D 7/12* (2006.01)
  *C08K 5/549* (2006.01)

(56) References Cited

U.S. PATENT DOCUMENTS

| | | | |
|---|---|---|---|
| 7,125,926 | B2 | 10/2006 | Satoh et al. |
| 8,276,664 | B2 * | 10/2012 | Gupta .................... C08B 1/003 166/278 |
| 9,249,313 | B2 * | 2/2016 | Haddad .................... C07F 7/21 |
| 2004/0209139 | A1 | 10/2004 | Extrand |
| 2007/0224391 | A1 | 9/2007 | Krupenkin et al. |
| 2008/0015298 | A1 | 1/2008 | Xiong et al. |
| 2008/0221262 | A1 | 9/2008 | Mabry et al. |
| 2012/0000853 | A1 * | 1/2012 | Tuteja .................... B01D 69/02 210/650 |
| 2012/0279575 | A1 | 11/2012 | Tronc et al. |
| 2013/0122225 | A1 | 5/2013 | Azimi et al. |
| 2013/0178568 | A1 | 7/2013 | Meuler et al. |

OTHER PUBLICATIONS

United States Patent and Trademark Office, Non-Final Office Action in U.S. Appl. No. 12/599,465, dated Sep. 31, 2012.
United States Patent and Trademark Office, Final Office Action in U.S. Appl. No. 12/599,465, dated Jan. 16, 2013.
United States Patent and Trademark Office, Non-Final Office Action in U.S. Appl. No. 12/599,465, dated May 15, 2014.
United States Patent and Trademark Office, Final Office Action in U.S. Appl. No. 12/599,465, dated Oct. 16, 2014.
United States Patent and Trademark Office, Non-Final Office Action in U.S. Appl. No. 12/599,465, dated Sep. 16, 2015.
United States Patent and Trademark Office, Final Office Action in U.S. Appl. No. 12/599,465, dated Jan. 25, 2016.
United States Patent and Trademark Office, Non-Final Office Action in U.S. Appl. No. 13/734,446, dated May 1, 2015.
United States Patent and Trademark Office, Final Office Action in U.S. Appl. No. 13/734,446, dated Nov. 23, 2015.
United States Patent and Trademark Office, Non-Final Office Action in U.S. Appl. No. 13/734,446, dated Jun. 10, 2016.
M. J. Owen et al., "Surface active fluorosilicone polymers," Macromol. Symp., vol. 82 (1994) p. 115.
United States Patent and Trademark Office, International Search Report and Written Opinion in International Application No. PCT/US15/34407, dated Aug. 26, 2015.
Asahi Glass Co. Ltd., Material Safety Data Sheet for Asahiklin AK225, Oct. 31, 2011.
United States Patent and Trademark Office, Non-Final Office Action in U.S. Appl. No. 12/599,465, dated Aug. 19, 2016, 15 pages total.
United States Patent and Trademark Office, Non-Final Office Action in U.S. Appl. No. 14/732,652, dated Sep. 7, 2016, 10 pages total.
United States Patent and Trademark Office, Non-Final Office Action in U.S. Appl. No. 14/732,652, dated Sep. 7, 2016, 8 pages total.
United States Patent and Trademark Office, Final Office Action in U.S. Appl. No. 14/732,652, dated Dec. 9, 2016, 6 pages total.
United States Patent and Trademark Office, Final Office Action in U.S. Appl. No. 12/599,465, dated Feb. 14, 2017, 13 pages total.

* cited by examiner

SYNTHESIS OF FUNCTIONAL FLUORINATED POLYHEDRAL OLIGOMERIC SILSESQUIOXANE ("F-POSS")

Pursuant to 37 C.F.R. §1.78(a)(4), this application is a divisional of U.S. application Ser. No. 13/624,151, filed Sep. 21, 2012, now U.S. Pat. No. 9,249,313, entitled SYNTHESIS OF FUNCTIONAL FLUORINATED POLYHEDRAL OLIGOMERIC SILSESQUIOXANE (F-POSS), which claimed the benefit of and priority to prior filed Provisional Application Ser. No. 61/537,122, filed Sep. 21, 2011. This application is related to U.S. application Ser. No. 14/662,305 filed Mar. 19, 2015; Ser. No. 13/624,355 filed on Sep. 21, 2012; and 61/537,125 filed Sep. 21, 2011.

The disclosures of these applications are expressly incorporated herein by reference, in their entireties.

RIGHTS OF THE

The invention described herein may be manufactured and used by or for the Government of the United States for all governmental purposes without the payment of any royalty.

FIELD OF THE INVENTION

The present invention relates generally to silsesquioxane materials and, more particularly to silsesquioxane materials having increased hydrophobicity.

BACKGROUND OF THE INVENTION

Polyhedral Oligomeric SilSesquioxanes ("POSS") are cage-structures having a silicon-oxide ($SiO_{1.5}$) core surrounded by aliphatic or aromatic organic functionality. One such POSS derivative, octakis(1H,1H,2H,2H-heptadecafluorodecyl) POSS ("F-POSS"), possesses a periphery of long-chain fluorinated alkyl groups and has been determined to possess the lowest surface energy value of any crystalline solid ($\gamma_{sv}$=9.3 mN/m). Superhydrophobic (contact angles of a water droplet exceeding 150°) and oleophobic (repelled by oil) surfaces have been produced by casting F-POSS materials onto a substrate or blending the F-POSS material into a polymer matrix.

Conventionally, F-POSS has been used as standalone compounds without further reactive chemical functionality; however, this absence of reactive chemical functionality limits solubility in common solvents, the mechanical robustness, and abrasion resistance of surfaces comprising these materials. One attempt to overcome such limitations has been an incompletely-condensed F-POSS compound with silanol functionality, which enabled new, robust, low surface energy hybrid materials. In fact, incompletely-condensed silsesquioxane frameworks have emerged with alkyl and/or aryl peripheries and are operable as synthons for creating hybrid inorganic-organic materials, as models for silica, for catalyst support, and as precursors for other silsesquioxane containing polymers.

Unfortunately, none of the conventional synthesis strategies are viable to produce long-chain (more than three carbon atoms) F-POSS compounds possessing additional reactive or non-reactive functionality beyond alkyl or aryl peripheries. Exemplary strategies, such as those described in U.S. Pat. No. 7,053,167, entitled SILSESQUIOXANE DERIVATIVE HAVING FUNCTIONAL GROUP, issued to Ito et al. on Apr. 8, 2004 and U.S. Pat. No. 7,291,747, entitled NOVEL SILICON COMPOUNDS AND PROCESS FOR PREPARATION THEREOF, issued to Oikawa et al. on Nov. 6, 2007 (disclosures incorporated herein by reference, in their entireties), have not produced long-chain F-POSS-$(ONa)_3$ having more than three carbon atoms. Modified methods have produced (3,3,3-trifluoropropyl)$_7$Si$_7$O$_9$(ONa)$_3$, which can be derivatized with long-chain fluorinated trichlorosilanes to produce low surface energy materials, but the trifluoropropyl groups are still limited in chain length.

While these conventional methods have proven successful for the synthesis of incompletely-condensed compounds possessing alkyl- and aryl-functionality, there remains a need for a method of synthesizing an incompletely-condensed, long-chain F-POSS compound.

SUMMARY OF THE INVENTION

The present invention overcomes the foregoing problems and other shortcomings, drawbacks, and challenges of synthesizing an incompletely-condensed, long-chain F-POSS compound. While the invention will be described in connection with certain embodiments, it will be understood that the invention is not limited to these embodiments. To the contrary, this invention includes all alternatives, modifications, and equivalents as may be included within the spirit and scope of the present invention.

A method of manufacturing a fluorinated polyhedral oligomeric silsesquioxane ("F-POSS") that has a chemical structure:

where $R_f$ represents a nonreactive, fluorinated organic group, $R_1$ represents a first monovalent organic group comprising at least two carbon atoms, and $R_2$ represents hydrogen or a second monovalent organic group comprising at least two carbon atoms. The method for manufacture includes opening a single edge of a closed-cage F-POSS and bridging the opened, single edge with a sulfate group. The sulfate group is converted to a disilanol, which is then reacted with a functional dichlorosilane having an organic functional group comprising at least three carbon atoms.

Still other embodiments of the present invention include a method of forming a hydrophobic and oleophobic surface by spin coating an inert surface with the F-POSS.

One embodiment of the present invention is directed to a method of manufacturing a fluorinated polyhedral oligomeric silsesquioxane ("F-POSS") that has a chemical structure:

where $R_f$ represents a fluorinated alkyl group, $R_1$ represents a first group having at least two carbon atoms, and $R_2$ represents hydrogen or a second group comprising at least two carbon atoms. The method for manufacture includes opening a single edge of a closed-cage F-POSS and bridging the opened, single edge with a sulfate group. The sulfate group is converted to a disilanol, which is then reacted with a functional dichlorosilane having an organic functional group comprising at least three carbon atoms.

The above and other objects and advantages of the present invention shall be made apparent from the accompanying drawings and the descriptions thereof.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Figure 1:
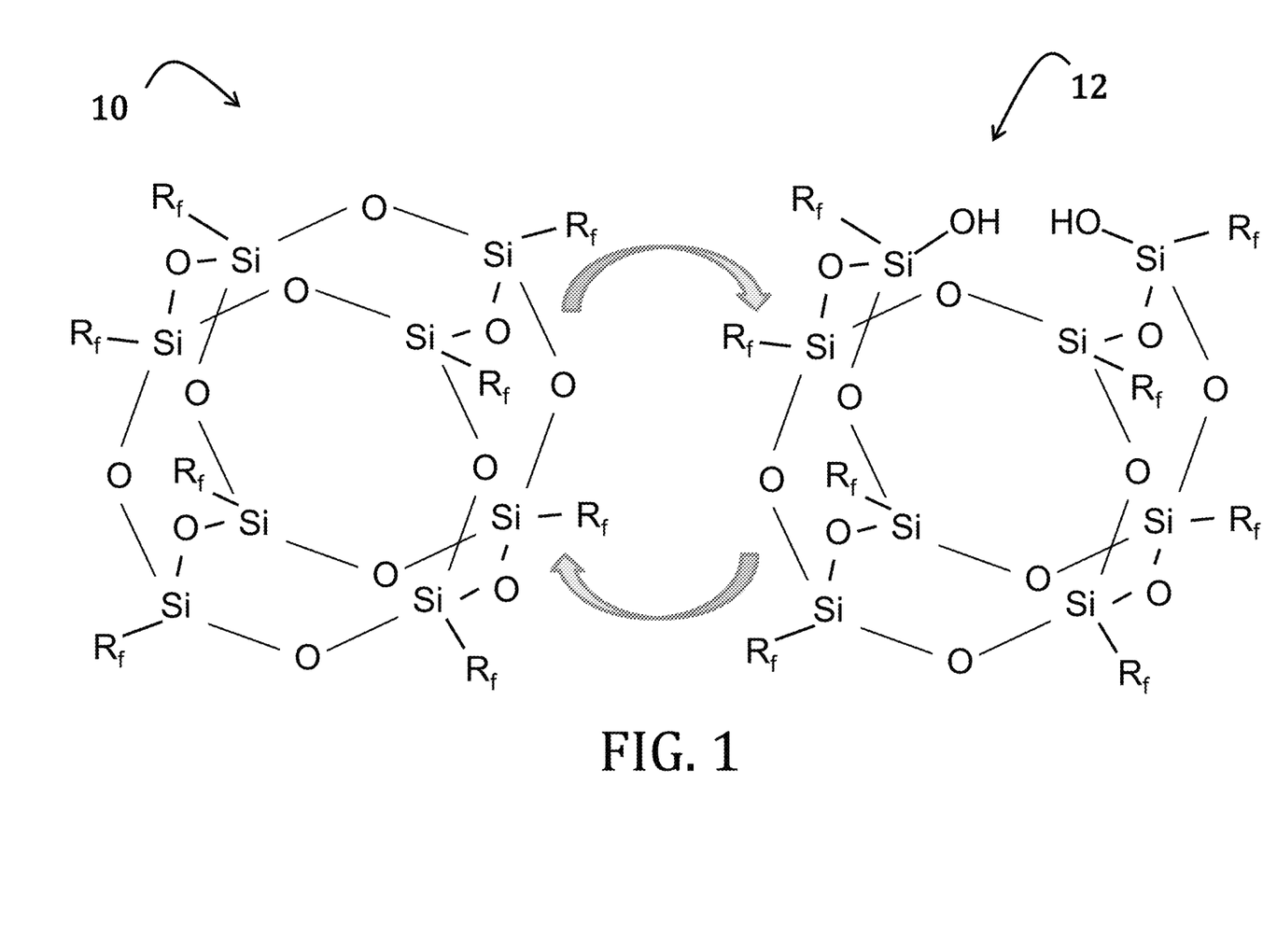
FIG. 1 is a schematic representation of the synthesis of one embodiment of an incompletely-condensed fluoroalkyl silsesquioxane.
Figure 2:
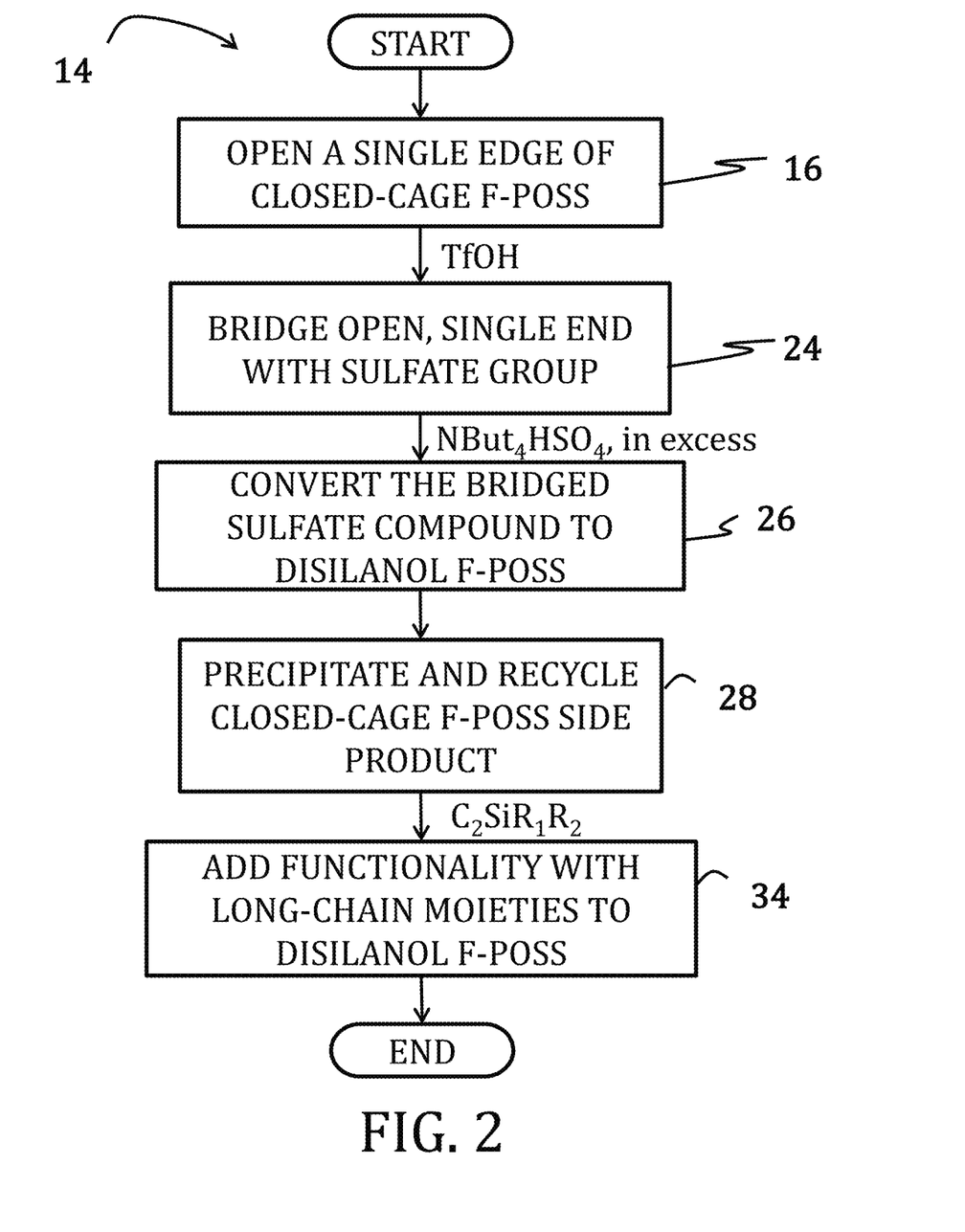
FIG. 2 is a flow chart illustrating a method of synthesizing an incompletely-condensed fluoroalkyl silsesquioxane in accordance with one embodiment of the present invention.

Turning now to the figures, and in particular to FIGS. 1 and 2, a multi-step synthetic method for converting a closed-cage F-POSS compound 10 to an incompletely-condensed silsesquioxane compound 12 (hereafter, "disilanol F-POSS" 12), $((R_f)_8Si_8O_{11}(OH)_2)$ is shown and described in detail. While not necessary, but for purposes of illustration, the F-POSS compound 10 includes nonfunctional groups, $R_f$, which may comprise —$CH_2CH_2(CF_2)_7(CF_3)$; however, other moieties, may also be included. Indeed, not all $R_f$ groups are required to have the same functionality.

Figure 3A:
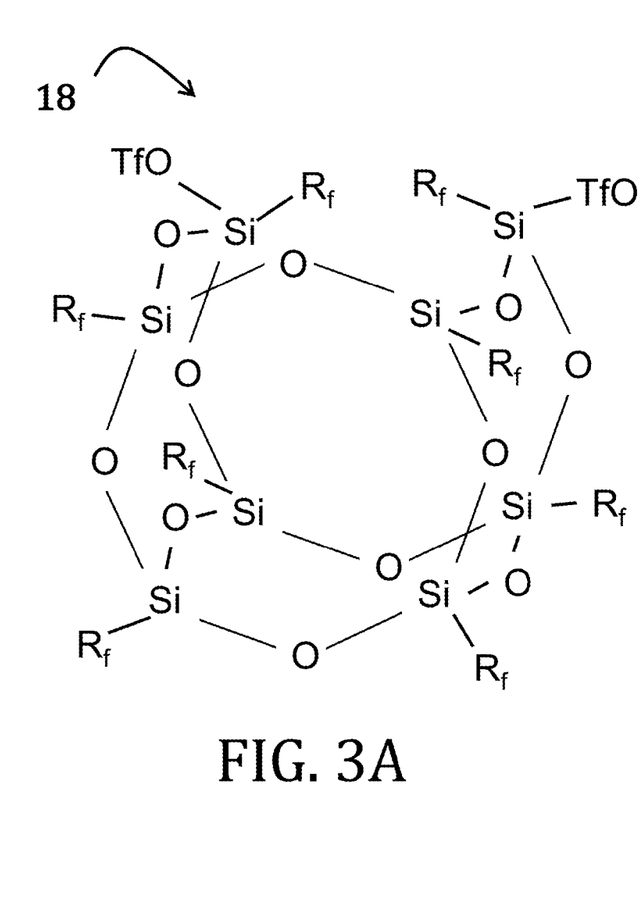
FIGS. 3A and 3B are schematic representations of two intermediates in the synthesis of FIG. 1.

More particularly, and as provided in the flow chart 14 of FIG. 2, a single edge of the closed-cage F-POSS compound is opened (Block 16) with trifluoromethane sulfonic acid, such as triflic acid ("TfOH"), in $C_6F_6$ and $CF_3SO_3H$ at 25° C. for 75 min. to form a first, unstable intermediate, which is illustrated herein as ditriflate POSS cage 18, $((R_f)_8Si_8O_{11}(OTf)_2)$, which is shown in FIG. 3A. Presence of the ditriflate POSS cage formation was confirmed, despite spectral complexity, via $^{29}Si$ NMR. The spectrum demonstrated an equilibrium between the open and closed-cage silsesquioxane frameworks 10, 18, with resonances at −62.6 ppm, −65.0 ppm, and −67.7 ppm and an integrated ratio of 2:2:4. While not wishing to be bound by theory, it is thought that the inability to isolate the first intermediate, ditriflate POSS 18, may be attributed to the strong electron-withdrawing effects of the fluorinated alkyl groups, $R_f$.

Figure 3B:
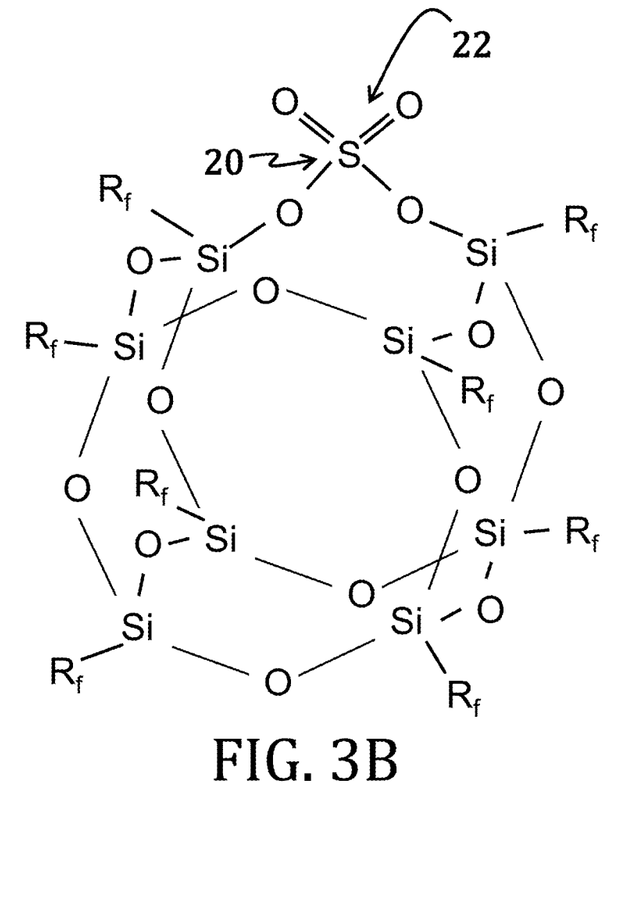

The open, single end of the ditriflate compound 18 may then be bridged with a sulfate group 20 to a second, unstable intermediate, a bridged sulfate compound 22 (FIG. 3B), $((R_f)_8Si_8O_{13}(SO_2))$, in Block 24 over a reaction time, for example, of approximately 30 min., with an excess of $NBut_4HSO_4$, under nitrogen. The reaction mixture separates into two liquid layers: a first, yellow aqueous layer and a second, colorless fluorinated solvent layer containing both of the closed-cage F-POSS compound 10 (FIG. 1) and the bridged sulfate compound 22. While the bridging sulfate moiety 20 appears to stabilize the electron-withdrawing F-POSS cage framework, the bridged sulfate compound 22 cannot be isolated. Its presence is confirmed, however, as another NMR-observed intermediate with $^{29}Si$ resonances at −64.5 ppm, −65.7 ppm, and −67.3 ppm with an integrated ratio of 2:2:4. Although the bridged sulfate compound 22 was not isolated, its endohedral geometry was deduced from x-ray crystallography data, described in detail below.

Referring again to FIG. 2, a polar fluorinated solvent/water mixture (for, example, a 10:1 ratio of solvent to water) is added to the fluorinated solvent layer (the colorless, aqueous layer above) of the reaction mixture for a time ranging from about 6 hours to about 12 hours to convert the bridged sulfate compound 22 to the disilanol F-POSS 12 of FIG. 1 (Block 26). Because the reaction requires water to be miscible with the fluorinated solvent, the polar fluorinated solvent/water mixture is necessary to yield the desired, disilanol compound.

To isolate the disilanol F-POSS 12, ethyl acetate is added to the reaction mixture, and subsequently filtered. The filtrate is collected, concentrated, suspended again in chloroform, and filtered. The collected filtrand is dried under vacuum (about 18 hours at 50° C.) to yield the product with an overall yield of approximately 53% and a molecular weight of 4009 g/mol.

The principle side product of the conversion (Block 26) is the closed cage F-POSS compound 10. Due to subtle differences in solubility between the closed cage F-POSS 10 and the disilanol F-POSS 12, disilanol F-POSS 12 may be purified from the closed cage F-POSS 10, the latter of which may be subsequently recycled (Block 28). In accordance with one embodiment of the present invention, the closed cage F-POSS 10 may be precipitated from the reacted polar fluorinated solvent/water mixture while the disilanol F-POSS 12 is subsequently precipitated from a $CHCl_3$ solution.

The structure of disilanol F-POSS 12 was determined by combustion analysis and multinuclear NMR ($^1H$, $^{13}C$, $^{19}F$, and $^{29}Si$). The $^{29}Si$ NMR spectrum displayed peaks at −59.0 ppm, −65.5 ppm, and −68.1 ppm, with an integration ratio of 2:2:4, which are attributed to the $C_{2v}$ symmetry of silsesquioxane. The peak at −59.0 ppm is attributed to the silanol groups of the POSS framework.

Figure 4:
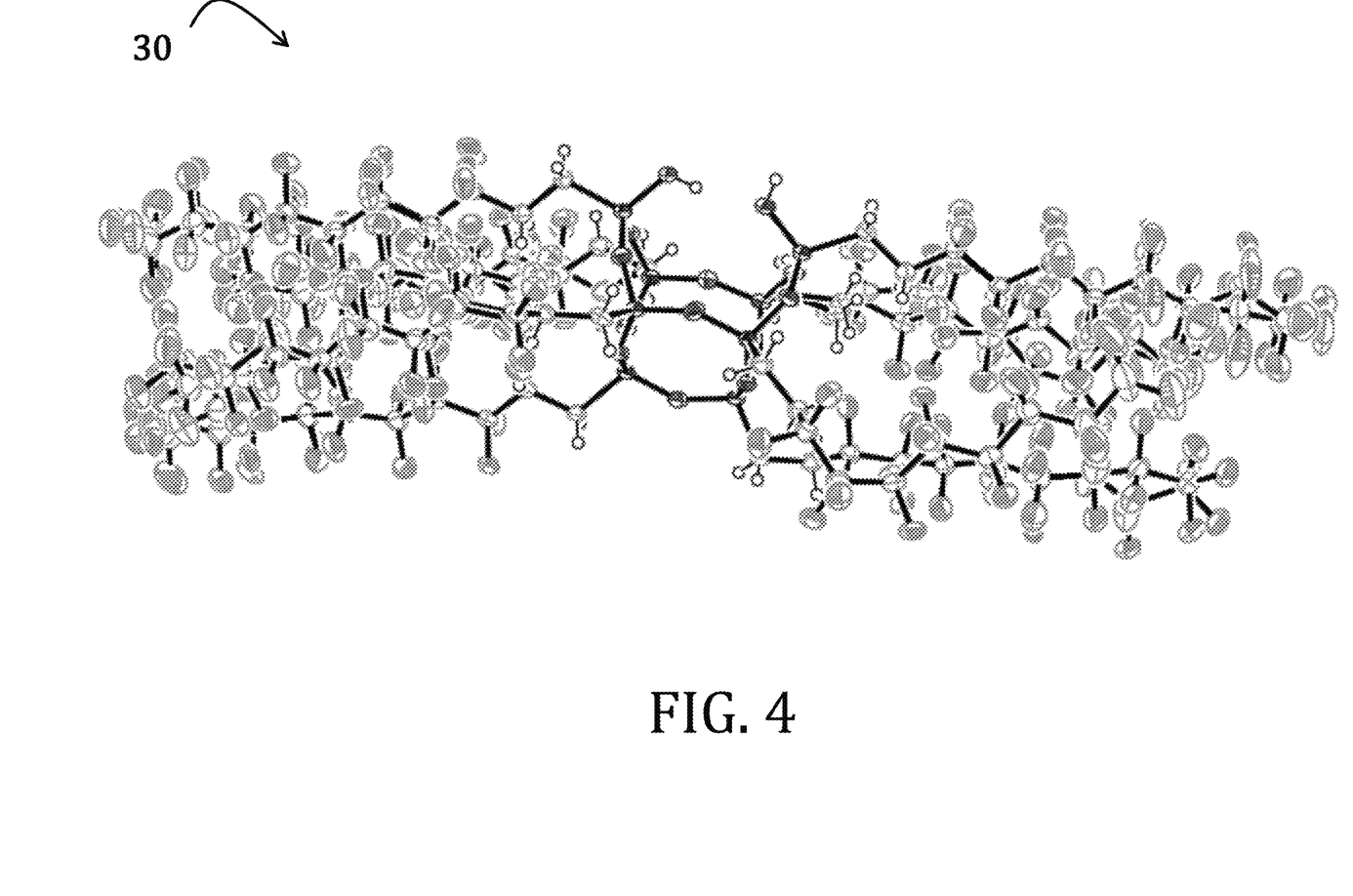
FIG. 4 is a schematic representation of a crystal structure determined for the incompletely-condensed fluoroalkyl silsesquioxane.

The crystal structure 30 for disilanol F-POSS 12, shown in FIG. 4, was obtained by growing crystals from slow evaporation in hexafluorobenzene and using a 3-circle SMARTAPEX CCD (Kusing Bruker, Billerica, Mass.) with c-axis fixed at 54.748 and temperature of about 100 K with SMART V 5.625 program. Graphite monochromated $Cu_{K\alpha}$ ($\lambda$=1.54179 Å) radiation was used for data collection, the SAINT V 6.22 program (Bruker, Corp.) was used for correcting Lorentz and polarization effects, and the SADABS program (Bruker, Corp.) was used for reflection scaling.

The structure was solved from $C_6F_6$ by direct methods (SHELXL-97, Bruker, Corp.) and all non-hydrogen atoms refined anisotropically using full-matrix, least squares refinement on $F^2$ and determined to be monoclinic P2(1)/c. The structure contains rigid, helical-like fluoroalkyl chains that are similar to the closed cage F-POSS 10 (FIG. 1) but are attached to the open Si—O frame-work by methylene groups. The crystal structure supports the 2:2:4 ratio of silicon atoms as determined by $^{29}$Si NMR spectroscopy of silicon atoms.

Figure 5:
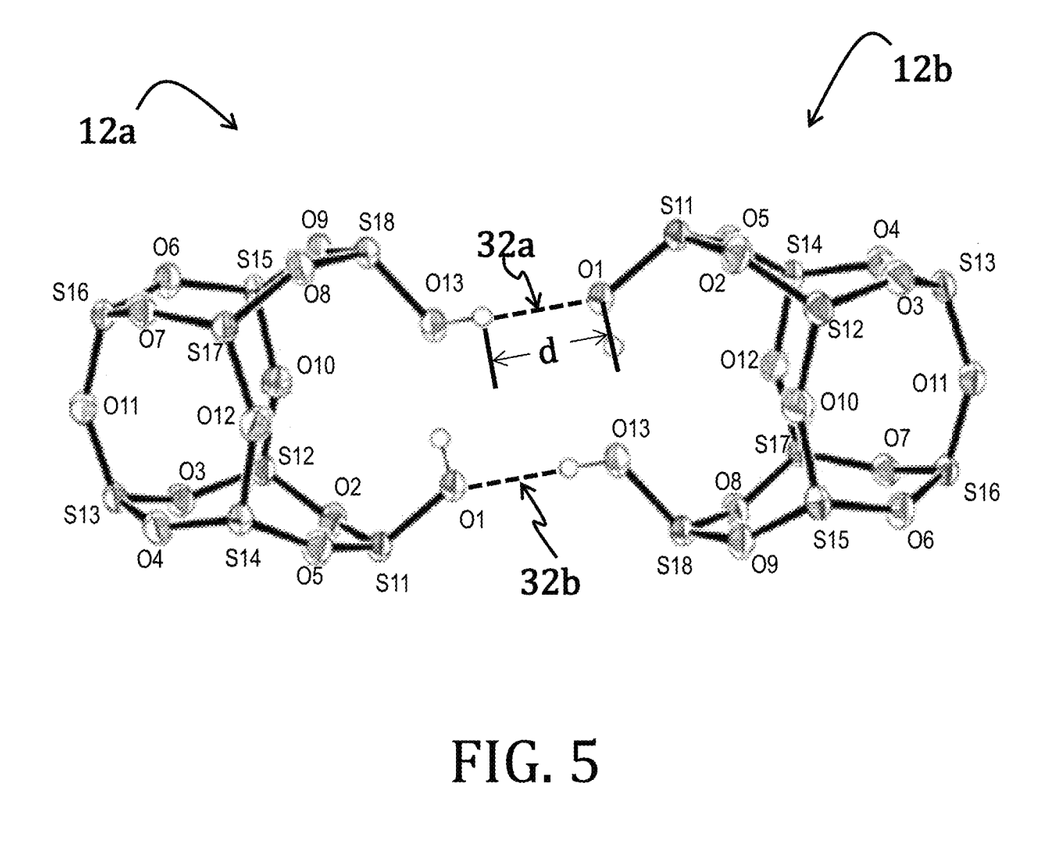
FIG. 5 is a schematic representation of a portion of the crystal structure of FIG. 4, showing the intermolecular hydrogen bonding.

The crystal packing of two disilanol F-POSS molecules (illustrated as 12a and 12b in FIG. 5, specifically, and in FIG. 6, generally, as crystal packing) reveals a dimeric structure with two F-POSS cages forming intermolecular hydrogen bonds 32a, 32b between silanol groups on of adjacent ones of the F-POSS cages 12a, 12b. This induces an increase in the lattice volume (approximately 12884 Å$^3$) for disilanol F-POSS 12 as compared to the volume of the closed cage F-POSS 10, which was approximately 6340 Å$^3$. Like the hydrogen bonding between silanols on incompletely-condensed alkyl based POSS triols and diols, a dimeric contact is established from intermolecular disilanol compounds at a distance, d, of approximately 2.798 Å. These intermolecular silanols are slightly closer than intramolecular silanols, (illustrated on FIGS. 5 as O1, O2, O3, O4, O5, O6, O7, O8, O9, O10, O11, O12, and O13), which are separated by a distance of approximately 2.810 Å. As described in detail below, the intermolecular silanols are reactive to chlorosilanes.

To achieve an effective convergence on the structure, certain restrains were applied, including, for example, as the thermal behavior of the structure (SIMU and DELU commands for Si1 to F36C); ISOR was applied to fluorine atoms due to the associated disorder, intermolecular distances (C—C and C—F) were retrained using the SAME command. After a stable minimum was achieved, hydrogen atoms were added at calculated positions to the alpha and beta carbon atoms. Hydrogen atoms on O1 and O13 were added using DFIX to restrain the distances (0.84 Å) to the respective oxygen atoms.

Additional details with respect to the crystal structure may be obtained from the Cambridge Crystallographic Data Centre, available at http://www.ccdc.com.ac.uk, Deposition Number 843485, the disclosure of which is incorporated herein by reference, in its entirety.

Figure 6:
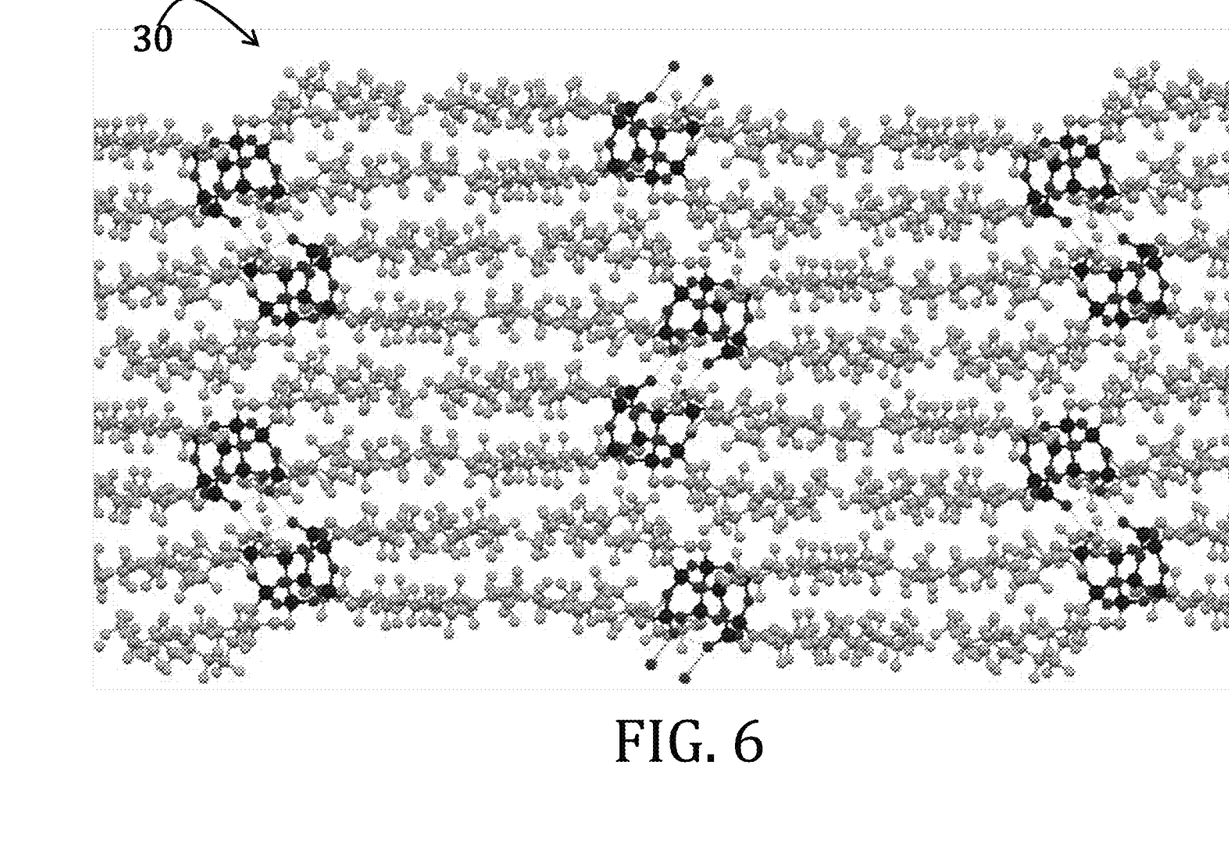
FIG. 6 is a schematic representation of crystal packing of a plurality of incompletely-condensed fluoroalkyl silsesquioxane, illustrating the hydrogen bonds between silanols.

Referring now to FIGS. 1, 2, and 6, disilanol F-POSS 12 is shown to readily react with functional dichlorosilanes ($Cl_2SiR_1R_2$) to add a particular or desired functionality (Block 34), which may include, for example, superhydrophobic or oleophobic properties. According to one embodiment of the present invention, the disilanol F-POSS 12 was condensed with bis(n-octyl)dichlorosilane in the presence of triethylamine to yield a functionalized F-POSS compound 36 (approximately 46% yield), shown in FIG. 7, with a loss of HCl. More particularly, bis(n-octyl)dichlorosilane and disilanol F-POSS 12, in $C_6F_6$, are mixed for 20 minutes and followed with the addition of triethylamine, in $C_6F_6$, and further mixing for about 12 hours. The solution is filtered and poured into ethyl acetate, causing white solid precipitate formation. Precipitate was removed via vacuum filtration, concentrated, dissolved in diethyl ether, and filtered again. The filtrate is then collected and cooled to 0° C., affording a white precipitate, which is collected and dried under vacuum to a white powder. The primary side product isolated during the reaction was, again, the closed cage F-POSS 10 (FIG. 1).

Figure 7:
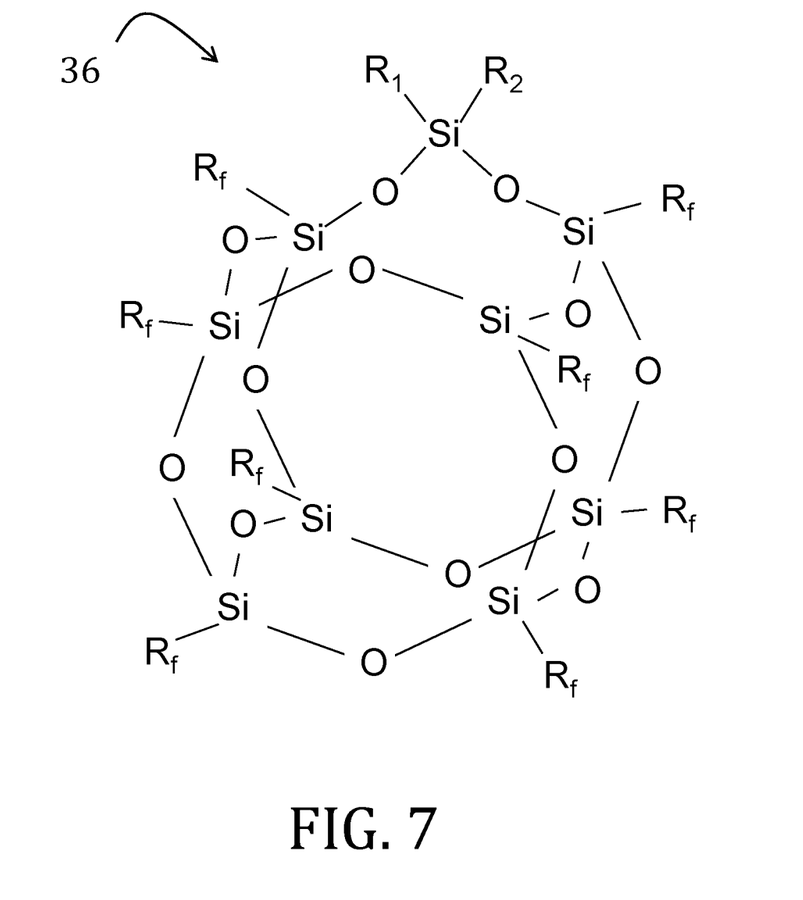
FIG. 7 is a schematic representation of the synthesis of one embodiment of a functionalized F-POSS compound.

Evaluation of the structure of the functionalized F-POSS compound 36 included multinuclear NMR ($^1$H, $^{13}$C, $^{19}$F, and $^{29}$Si), FT-IR, and combustion analysis. NMR spectra were obtained on 300 MHz and 400 MHz spectrometers (Bruker Corp.) using 5 mm o.d. tubes. An inverse gated 30° pulse with a 12 second delay was used to acquire the $^{29}$Si NMR spectra. The NMR spectrum produced $^{29}$Si resonances at −17.8 ppm, −65.4 ppm, −68.2 ppm, and −69.0 ppm, with a ratio of 1:2:4:2, of which the resonance at −17.8 ppm was attributed to dioctyl-functionalized Si atom. Large C—H stretches observed at 2974 cm$^1$ and 2871 cm$^{-1}$ in the FT-IR spectrum (Perkin Elmer Spectrum BX; Waltham, Mass.) supported the presence of the hydrocarbon chains, $R_1$, $R_2$.

As described herein, incompletely-condensed disilanol F-POSS compounds may be synthesized from fully condensed F-POSS compounds via a three-step reaction process and are reactive toward dichlorosilanes to produce a functional F-POSS compound. Crystal structures demonstrate silanol groups are hydrogen bonded via intermolecular interaction, which lowers the surface energy value beyond values observed with alkyl or aryl F-POSS compounds. Accordingly, the novel, tunable structure of the functionalized F-POSS compounds described herein provides unprecedented access to fluorinated building blocks for manufacturing low surface energy materials that are mechanically robust and abrasion resistant. For example, functionalized F-POSS 36 may be cast onto a substrate or blended with copolymers to produce surfaces having robust, abrasion resistant, superhydrophobic, and oleophobic material properties.

The following examples and comparative example illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

EXAMPLE 1

Seven, long-chain F-POSS compounds, each having a different functional group, were prepared in accordance with embodiments of the present invention. The F-POSS compounds included F-POSS (no additional functional group), dihydroxy silyl F-POSS (Si—(OH)$_2$), dioctyl silyl F-POSS (Si—((CH$_2$)$_7$CH3)$_2$), dihexyl silyl F-POSS (Si—(C$_6$H$_5$)$_2$), vinyl methylsilyl F-POSS (Si—(CH$_3$)(CH=CH$_2$)), acrylate methylsilyl F-POSS (Si—((CH$_3$((CH$_2$)$_3$OC(O)CCH=CH$_2$)), and methylacrylate methylsilyl F-POSS (Si—(CH$_3$)((CH$_2$)$_3$OC(O)C(CH$_3$)=CH$_2$)). The synthesis of each compound was confirmed using combustion analysis, FT-IR, and multinuclear NMR spectroscopy.

The long-chain fluoroalkyl periphery on F-POSS results in desirable low surface energy characteristics. Interestingly, once a non-fluorinated segment was added to an edge of F-POSS, the solubility properties change dramatically. For example, the long hydrocarbon chains present in dioctyl silyl F-POSS expanded solubility from just fluorinated solvents to include non-fluorinated solvents, such as $Et_2O$ and $CHCl_3$. Even small organic modifications, such as the acrylate and methacrylate moieties on acrylate methylsilyl F-POSS and methylacrylate methyl silyl F-POSS, respectively, were sufficient to expand solubility to nonfluorinated solvents, such as $Et_2O$. However, phenyl and vinyl groups of dihexyl silyl F-POSS and vinyl methylsilyl F-POSS, respectively, did not improve the solubility in non-fluorinated solvents, which may be attributed to the rigidity of the phenyl and vinyl groups.

Films of each of the seven F-POSS compounds were spin cast onto seven wafers (1 inch silicon) from solutions of Asahiklin-255 (3,3-dichloro-1,1,1,2,2,-pentafluoropropane/1,3-dichloro-1,1,2,2,3-pentafluoropropane) (10 mg/mL) at a rate of 900 rpm for 30 seconds and in accordance with the methods described in S. S. CHHATRE et al. "Fluoroalkylated Silicon-Containing Surfaces—Estimation of Solid-Surface Energy," *ACS Appl. Mater. Interfaces*. Vol. 2 (2010) 3544-3554, the disclosure of which is incorporated herein by reference, in its entirety. Dihydroxy silyl F-POSS was spin cast in a similar manner but from $C_6F_6$ solution at a rate of 1400 rpm. Surfaces were smoothed to less than 5 nm rms roughness to minimize any influence of surface roughness and topology as measured via atomic force microscopy using a Nanoscope IV (Digital Instruments, Inc., whole-owned subsidiary of Veeco Instruments, Inc., Plainview, N.Y.) and optical profilometry using a Wyko NT930 (Veeco Instruments, Inc.).

The influence of functionality on non-wetting behavior was determined by examining static and dynamic contact angles of water and hexadecane on each F-POSS film surface. Water and hexadecane 10 μL droplets were positioned on the prepared wafers. Dynamic contact angles were determined by placing a 3 μL drop of the probing liquid onto a test substrate of a DataPhysics OCA20 goniometer (DataPhysics Instruments GmbH, Filderstadt, Germany). An additional 2 μL of the probing liquid was added through a dispending needle at a rate of 0.2 μL/sec and then 3 μL removed at 0.2 μL/sec. Video (ranging from 20 frames to 100 frames) was captured during the addition and removal of the probing liquid such that advancement and recession of a contact line between the droplet and the test substrate, respectively, was observed and used for determining the advancing and receding contact angles, respectively. Measurements were made from a "tangent lean" fit using a droplet fitting software (DataPhysics Instruments GmbH).

The open-cage framework of compound dihydroxy silyl F-POSS did not display any adverse effect on the wetting behavior, which was attributed to the dimeric structure formed with silanols shielded from the surface of the film. A slight increase in contact angle hysteresis, $\theta_{rec}-\theta_{adv}$, for dioctyl silyl F-POSS, vinyl methylsilyl F-POSS, acrylate methylsilyl F-POSS, and methylacrylate methylsilyl F-POSS was observed when wetted with water. This slight increase was not observed for surfaces comprising the same films when wetted with hexadecane, except for dioctyl silyl F-POSS. The structure of dioctyl silyl F-POSS contains long aliphatic chains that potentially favor interaction with a long-chain organic solvent, such as hexadecane.

Dihydroxy silyl F-POSS and dihexyl silyl F-POSS displayed the lowest hexadecane hysteresis values of all film surfaces and possessed sliding angles of approximately 7°. These initial measurements demonstrate that modifications of the F-POSS structure were found to be influential on wetting properties, either increasing or decreasing contact angle hysteresis.

TABLE 1

| LONG-CHAIN F-POSS | WATER | | HEXADECANE | |
|---|---|---|---|---|
| | ($\theta_{adv}$, degrees) | ($\theta_{rec}$, degrees) | ($\theta_{adv}$, degrees) | ($\theta_{rec}$, degrees) |
| F-POSS | 124.0 ± 0.5 | 109.6 ± 0.7 | 79.1 ± 0.4 | 65.1 ± 0.5 |
| Dihydroxy silyl F-POSS | 116.8 ± 0.4 | 111.0 ± 0.6 | 77.4 ± 0.4 | 74.4 ± 0.8 |
| Dioctyl silyl F-POSS | 117.9 ± 0.5 | 95.5 ± 0.4 | 69.1 ± 1.2 | 23.1 ± 1.2 |
| Dihexyl silyl F-POSS | 116.2 ± 0.4 | 110.5 ± 0.5 | 76.0 ± 0.8 | 73.2 ± 0.4 |
| Vinyl methylsilyl F-POSS | 116.2 ± 0.4 | 100.6 ± 0.8 | 78.4 ± 0.3 | 70.6 ± 2.3 |
| Acrylate methylsilyl F-POSS | 118.2 ± 1.0 | 90.6 ± 1.0 | 76.8 ± 0.3 | 67.8 ± 1.0 |
| Methylacrylate methylsilyl F-POSS | 117.0 ± 0.6 | 93.8 ± 1.5 | 78.1 ± 0.4 | 63.0 ± 1.2 |

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A method of manufacturing a fluorinated polyhedral oligomeric silsesquioxane ("F-POSS") having a structure:

where each $R_f$ represents a nonreactive, fluorinated organic group, $R_1$ represents a first monovalent organic group comprising at least two carbon atoms, and $R_2$ represents hydrogen or a second monovalent organic group comprising at least two carbon atoms, the method comprising:
   opening a single edge of a closed-cage F-POSS;
   bridging the opened, single edge with a sulfate group;
   converting the sulfate group to a disilanol; and
   reacting the disilanol with a functional dichlorosilane, the dichlorosilane having an organic functional group comprising at least three carbon atoms.

2. The method of claim 1, wherein the method of manufacturing is performed in $C_6F_6$ at for approximately 12 hours.

3. The method of claim 1, wherein opening the single edge of the closed-cage F-POSS includes reacting the closed-cage F-POSS with triflic acid.

4. The method of claim 1, wherein bridging the opened, single edge includes reacting the opened, single edge with $NBut_4HSO_4$.

5. The method of claim 1, wherein converting the sulfate group to a disilanol includes reacting the sulfate group with an excess solution of fluorinated solvent and water.

6. The method of claim 1, wherein $R_f$ represents —$CH_2CH_2(CF_2)_7CF_3$.

7. The method of claim 1, wherein $R_1$ is selected from the group consisting of —$(CH_2)_7CH_3$, —$(CH_2)_3OC(O)CH=CH_2$, and —$(CH_2)_3OC(O)C(CH_3)=CH_2$.

8. The method of claim 1, wherein the first monovalent organic group, the second monovalent organic group, or both comprises at least three carbon atoms.

9. The method of claim 1, wherein $R_f$ represents a fluorinated alkyl group.

10. The method of claim 1, wherein each $R_f$ is separately selected from the group consisting of fluorotetradecyl, fluorododecyl, fluorodecyl, fluorooctyl, fluorohexyl, and hexafluoro-i-butyl.

11. A method of manufacturing a fluorinated polyhedral oligomeric silsesquioxane ("F-POSS") having a structure:

where each $R_f$ represents a fluorinated alkyl group, $R_1$ represents a first group having at least two carbon atoms, and $R_2$ represents hydrogen or a second group comprising at least two carbon atoms, the method comprising:

opening a single edge of a closed-cage F-POSS;

bridging the opened, single edge with a sulfate group;

converting the sulfate group to a disilanol; and reacting the disilanol with a functional dichlorosilane, the dichlorosilane having an organic functional group comprising at least three carbon atoms.

12. The method of claim 11, wherein the method of manufacturing is performed in $C_6F_6$ at for approximately 12 hours.

13. The method of claim 11, wherein opening the single edge of the closed-cage F-POSS includes reacting the closed-cage F-POSS with triflic acid.

14. The method of claim 11, wherein bridging the opened, single edge includes reacting the opened, single edge with $NBut_4HSO_4$.

15. The method of claim 11, wherein converting the sulfate group to a disilanol includes reacting the sulfate group with an excess solution of fluorinated solvent and water.

16. The method of claim 11, wherein each $R_f$ is separately selected from the group consisting of fluorotetradecyl, fluorododecyl, fluorodecyl, fluorooctyl, fluorohexyl, and hexafluoro-i-butyl.

* * * * *